United States Patent [19]

Segawa et al.

[11] Patent Number: 5,028,735
[45] Date of Patent: Jul. 2, 1991

[54] PURIFICATION AND PREPARATION PROCESSES FOR METHYL METHACRYLATE

[75] Inventors: Hirozo Segawa, Kitakanbara; Norio Ishikawa; Katsuji Yoguchi, both of Takaishi; Morimasa Kuragano; Minoru Koshibe, both of Sakai, all of Japan

[73] Assignees: Mitsui Toatsu Chemicals, Inc., Tokyo; Kuraray Company, Ltd., Kurashiki, both of Japan

[21] Appl. No.: 501,716

[22] Filed: Mar. 30, 1990

[30] Foreign Application Priority Data

Mar. 31, 1989 [JP] Japan ................................. 1-78174

[51] Int. Cl.⁵ ........................ B01D 3/36; C07C 67/54
[52] U.S. Cl. .................................... 560/218; 203/37; 203/70; 203/74; 203/76; 203/81; 203/83; 203/DIG. 21; 568/916
[58] Field of Search ...................... 203/33, 29, 36, 37, 203/39, 70, 74, 81, 18, 76, 83, DIG. 21, 53; 560/218, 215; 568/916

[56] References Cited

U.S. PATENT DOCUMENTS

| | | | |
|---|---|---|---|
| 2,406,561 | 8/1946 | Rehberg | 560/218 |
| 2,614,072 | 10/1952 | Carlson et al. | 203/37 |
| 3,960,672 | 6/1976 | Ester et al. | 203/18 |
| 3,990,952 | 11/1976 | Katzen et al. | 203/37 |
| 4,518,462 | 5/1985 | Aoshima et al. | 203/70 |
| 4,791,221 | 12/1988 | Gabillet | 560/218 |

FOREIGN PATENT DOCUMENTS

| | | | |
|---|---|---|---|
| 51-108004 | 9/1976 | Japan | 568/916 |
| 58-203940 | 11/1983 | Japan | 560/218 |
| 62-123150 | 6/1987 | Japan | 560/218 |
| 935543 | 8/1963 | United Kingdom | 560/218 |

Primary Examiner—Wilbur Bascomb
Attorney, Agent, or Firm—Oblon, Spivak, McClelland, Maier & Neustadt

[57] ABSTRACT

A purification process for methyl methacrylate (MMA) and a recovery process for methanol are disclosed. A mixture, which contains water, methanol and methyl methacrylate (MMA) as principal components along with at least one of methyl acrylate, methyl propionate and methacrylic acid, is azeotropically distilled together with hexane to obtain MMA in a form substantially free of water, methanol methyl acrylate, methyl propionate and hexane and a low boiling-point fraction. The low boiling-point fraction is cooled and separated into a water phase and an oil phase. Methanol can be recovered from the water phase by adding an alkaline substance to it and then distilling the resultant mixture. A preparation process of MMA is also disclosed. MMA can be prepared by esterifying methacrylic acid or methacrylamide with methanol and then applying the above purification process.

7 Claims, 1 Drawing Sheet

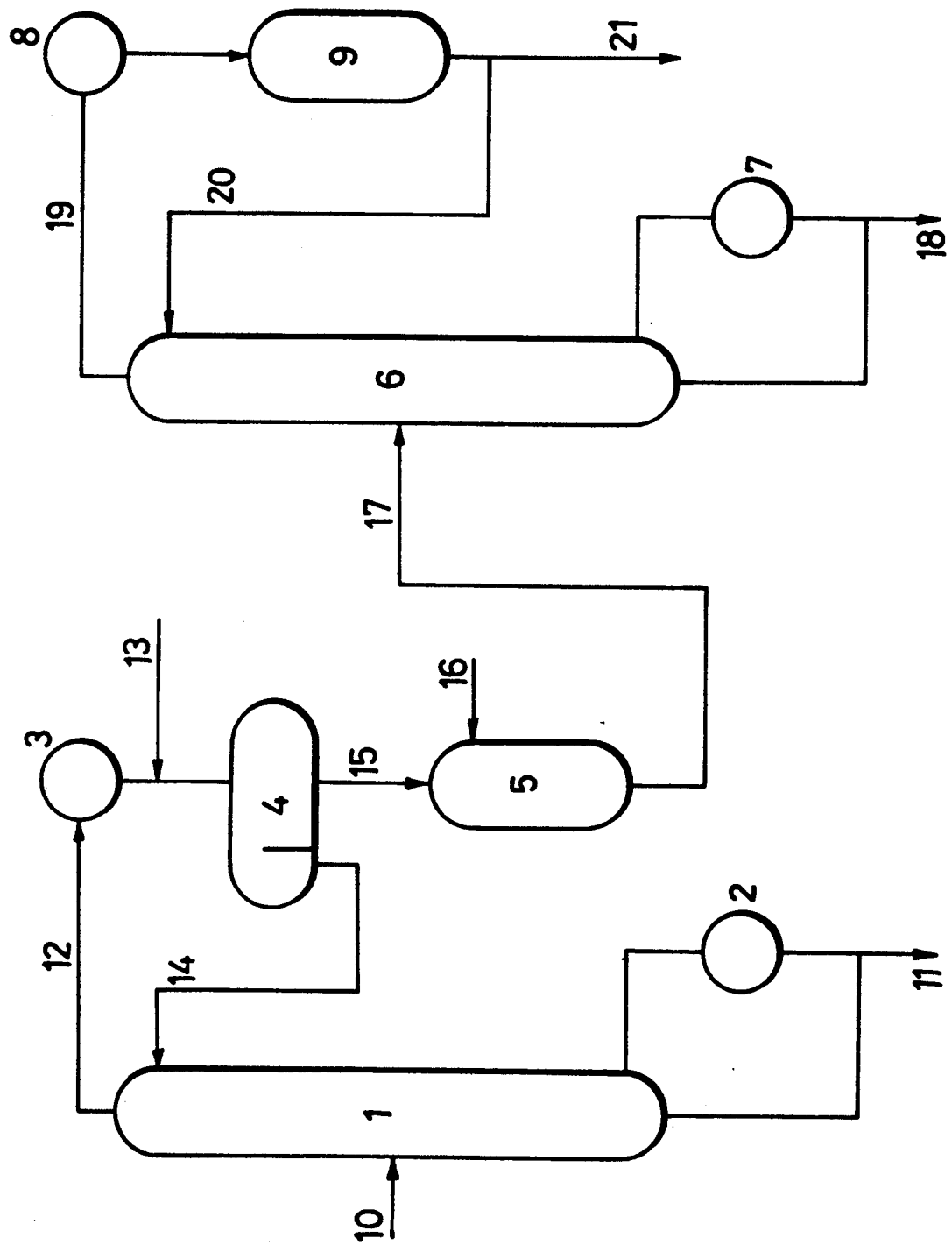

PURIFICATION AND PREPARATION PROCESSES FOR METHYL METHACRYLATE

BACKGROUND OF THE INVENTION

1. Field of the Invention

The present invention relates to a purification process for methyl methacrylate (hereinafter may be abbreviated as "MMA") and also to a preparation process for MMA.

2. Description of the Prior Art

MMA is produced by esterifying methacrylic acid (hereinafter may be abbreviated as "MAA") or methacrylamide with methanol in the presence of sulfuric acid, a strongly acidic ion-exchange resin or the like.

Crude MMA which is obtained from this esterification process contains, in addition to water formed by the reaction and unreacted methanol and MAA, small amounts of lower boiling-point impurities, such as methyl acrylate (hereinafter may be abbreviated as "MA") and methyl propionate (hereinafter may be abbreviated as "MP"), derived from impurities in the raw materials.

It is however difficult to recover MMA from crude MMA by conventional distillation procedures because MMA is close in boiling point to these impurities or MMA forms an azeotrope with them.

As a method for separating MMA from crude MMA, it has been proposed, for example, (1) to remove methanol from crude MMA by the azeotropic distillation which uses a hydrocarbon (Japanese Patent Laid-Open Nos. 9740/1982, 180457/1983 and 203940/1983), (2) to remove methanol from crude MMA by the extractive distillation in which water is used as a solvent (Japanese Patent Laid-Open No. 24812/1979), or (3) to extract and separate MMA by using water and a hydrocarbon as extracting solvents (Japanese Patent Laid-Open No. 24814/1979).

With the development of optoelectronics in recent years, methacrylic resins are now increasingly used in a large volume in the above field of art. There is hence an increasing demand for the quality of high purity from the standpoint of optical performance, to say nothing of the standpoint of mechanical and chemical performance. However, the conventional preparation processes of MMA are not fully satisfactory not only from the process aspect but also from the economical aspect Moreover, impurities which would cause problems for the preparation of high-purity MMA cannot be fully removed even by these processes. Valuable components are usually recovered and recycled for reuse from the economical standpoint, especially in industrial processes. Impurities therefore gradually build up in the processes and may cause a quality reduction of the products unless their removal is perfect, even if they are contained in minute quantities in the raw materials.

SUMMARY OF THE INVENTION

It is the general object of the present invention to solve the above-described problems of the prior art techniques by providing an MMA preparation process which allows to obtain high-purity MMA in a higher yield than the conventional MMA preparation processes.

An object of the present invention is to provide a process for the purification of MMA, which can almost completely remove low boiling-point impurities such as water, methanol, MA and MP without losing MMA, and also to furnish a process for preparing MMA by making use of the above purification process.

Another object of the present invention is to provide a process for the recovery of methanol as a raw material for the preparation of MMA, which enables the recovery of methanol in a form free of detrimental impurities such as MA and MP, and also to furnish processes for purifying and preparing MMA by using the above recovery process.

To achieve the objects and in accordance with the purpose of the invention, as embodied and broadly described herein, the present invention provides a purification process of MMA, which can be suitably applied for the preparation of MMA, namely, a process for the purification of methyl methacrylate, which comprises the following steps:

azeotropically distilling, together with hexane, a mixture comprising water, methanol and MMA as principal components and containing at least one of MA, MP and MAA, thereby obtaining a high boiling-point fraction and a low boiling-point fraction, said high boiling-point fraction being substantially free of water, methanol, MA, MP and hexane and composed principally of MMA, said low boiling-point fraction being principally composed of water, methanol and hexane and containing at least one of MA and MP;

cooling the low boiling-point fraction to obtain a condensate;

separating the condensate into a water phase and an oil phase;

adding an alkaline substance to the water phase;

distilling the water phase which has been added with the alkaline substance, thereby recovering methanol; and using the oil phase as a source for hexane to be used in the azeotropic distillation.

The present invention also provides a recovery process of methanol, which can be suitably applied for the purification and preparation of MMA, namely, a process for the recovery of methanol from a mixture comprising water and methanol as principal components and containing at least one of MA and MP, which comprises adding an alkaline substance to the mixture and then distilling the resultant mixture.

The present invention further provides a process for the preparation of MMA, which comprises esterifying with methanol at least one methacrylic compound selected from the group consisting of MAA and methacrylamide, thereby obtaining a mixture comprising water, methanol and MMA as principal components and containing at least one of MA, MP and MAA; and then subjecting the mixture to the above MMA purification process including the above recovery of methanol.

Hexane useful in the practice of the present invention forms a minimum boiling point azeotrope with water and methanol, which are both contained in crude MMA. Hexane therefore facilitates the removal of these impurities.

The following problems will arise if crude MMA should be distilled without hexane. MMA itself acts as an entrainer and is hence azeotropically distilled together with water and methanol. As a result, MMA which is polymerizable is recirculated inside a distillation column, so that troublesome polymerization tends to occur therein. Further, a condensate which is obtained by condensing a top distillate can hardly be separated into a water phase and an oil phase, because the difference in specific gravity between these phases is small. In addition, impurities such as MA and MP in the condensate are distributed at only small rates into the water phase. As a result, only small portions of these impurities are discharged out of the system along with the water phase and impurities are therefore recirculated and accumulated in increasing quantities in the system.

These drawbacks can be overcome by using hexane as an entrainer. In this case, top distillate, in other words, overhead vapor is distilled out at a lower temperature and moreover, substantially no MMA is contained therein. The troublesome polymerization can therefore be minimized. The condensate of the top distillate can be easily separated into a water phase and an oil phase because there is a substantial difference in specific gravity between these phases. Further, the distribution of low boiling-point impurities, such as MA and MP into the water phase has been favorably improved, whereby the discharge of impurities to the outside of the system is facilitated.

The water phase which is discharged out of the system of the distillation column contains methanol useful as a raw material for the esterification. It is however impossible to recover methanol alone by distillation, because methanol and MA or MP mutually form a minimum boiling point azeotrope.

The present invention is also concerned with the effective process for the recovery of methanol from the water phase. The water phase is first treated with an alkaline substance, followed by distillation. This has made it possible to recover, as a raw material for the preparation of MMA, methanol in a form free of detrimental impurities. It is also feasible to avoid the accumulation and recirculation of MA and MP in the process.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

BRIEF DESCRIPTION OF THE DRAWING

FIG. 1 is a flow diagram of a purification plant employed in an example of the present invention.

DETAILED DESCRIPTION OF THE INVENTION

Reference will now be made in detail to the present preferred embodiments of the invention.

In the present invention, the term "crude MMA" means crude MMA obtained by esterifying MAA and/or methacrylamide with methanol The esterification is conducted at 60°-130° C. It is desired from the standpoints of process simplification and energy consumption to provide crude MMA for the purification process of the present invention after partly or substantially removing water, methanol and MAA therefrom by a conventional process. Crude MAA subjected to the purification process of the present invention may preferably be a mixture containing 2-10% (by weight; all designations of "%" will hereinafter mean wt. %) of water, 2-15% of methanol, not more than 2% of MAA, not more than of 1% of MA or MP, and 75-95% of MMA.

Crude MMA is distilled in the presence of hexane by a distillation means led by a distillation column. Upon conducting this distillation, it is necessary to use hexane in an amount sufficient to distill out water, methanol and the like, which are contained in the crude MMA, by the azeotropic distillation. In practice, it is only necessary to replenish hexane to the distillation column by recycling an oil phase, which is separated from a low boiling-point fraction, to the distillation column as will be described herein. The amount of hexane to be replenished to the distillation column preferably ranges from the sum of a 17-fold amount by weight of water and a 3-fold amount of methanol to the sum of a 50-fold amount by weight of water and a 10-fold amount of methanol. If hexane is replenished in an amount smaller than the lower limit, MMA is also distilled in the top distillate. It is hence not preferable to replenish hexane in such a small amount. No additional merit is brought about from the use of hexane in an amount greater than the upper limit, although no problem or inconvenience arises.

It is preferable to conduct the distillation under normal or reduced pressure. To prevent polymerization of MMA, it is desired to lower the operation pressure. However, an unduly low operation pressure results in such problems that large facilities are needed and a low-temperature cooling medium has to be used because of a reduction in the condensation temperature of the low boiling-point fraction. It is therefore preferable to conduct the distillation in a pressure range of 300–760 mm Hg. Under such pressures, the top temperature ranges from 37° C. to 63° C.

A bottom substantially free of water, methanol, MA and MP is obtained as a high boiling-point fraction from the bottom of the distillation column. Although this high boiling-point fraction still contains MAA and high boiling-point impurities in small amounts, high-purity MMA can be obtained by subjecting it to distillation again because impurities having boiling points close to MMA and water capable of forming an azeotropic mixture with MAA around the boiling point of MMA have already been removed.

The low boiling-point fraction composed principally of hexane is cooled and condensed, preferably at 5°-35° C. and then separated into a water phase and an oil phase in a reflux drum. Difficulties may be encountered upon separation of the condensate when the water content of the crude MMA employed as the raw material is low. Even in such a case, a water phase can still be formed by adding water to the reflux drum. A majority of hexane is distributed to the oil phase, whereas majorities of water and methanol are distributed to the water phase. Impurities such as MA and MP are distributed to both phases in accordance with their respective distribution coefficients. Here, the addition of water is effective not only in facilitating the separation of the condensate into two phases but also in reducing the concentrations of methanol, MA and MP in the oil phase. By recycling the hexane-rich oil phase to the distillation column, it is possible to minimize the amount of hexane to be used and also to achieve the effective removal of impurities.

By discharging the water phase out of the system, the low boiling-point impurities separated from crude MMA, such as MA and MP, can be removed along with water.

Methanol is recovered by treating this water phase with an alkaline substance and then distilling the resultant mixture. As the alkaline substance, sodium hydroxide or potassium hydroxide can be used preferably. The alkaline substance is added in an amount required to hydrolyze the above carboxylate esters contained in the water phase, namely, MA, MP and the like into their corresponding carboxylate salts. Preferably, the alkaline substance is used in a molar amount 1-2 times the sum of these carboxylate esters. The alkaline substance can be added at any stage before the water phase separated in the reflux drum is subjected to distillation for the recovery of methanol. The hydrolysis reactions are completed while the water phase remains within the distillation column. To promote the hydrolysis of such carboxylate esters, it is desirable to supply the water phase, to which the alkaline substance has been added, to the distillation column after subjecting the water phase to heat treatment at room temperature to 60° C. in advance. The distillation for the recovery of methanol is conducted under normal pressure, whereby methanol free of MA and MP can be recovered as a low boiling-point fraction.

This invention will hereinafter be illustrated by way of the following example, which is intended to be purely exemplary of the invention. The purification plant illustrated in FIG. 1 was employed.

Crude MMA containing water, methanol, MA, MP and MAA was fed through a feed line 10 to a middle stage of a first distillation column 1 (inner diameter: 150 mm; height: 10 m; packings: ¼″ Berl saddles). Heat was supplied at the base of column 1 through heat exchanger or reboiler 2. The crude MMA was distilled under the conditions that the operation pressure, top temperature and bottom temperature were controlled at 500 mm Hg, 54° C. and 90° C., respectively and the oil phase distilled was recycled in toto. The water, methanol, MA and MP, which were contained in the crude MMA as the feed material, were distilled out along with hexane, which has been fed through a feed line 14, through a line 12 by way of the top. The top distillate was condensed in a condenser 3 and then separated together with water, which has been fed through a feed line 13, into two layers in a reflux drum 4. An oil phase composed primarily of hexane was recycled to an upper stage of the first distillation column 1, while a water phase composed principally of water was discharged to a next hydrolysis tank 5 by way of a line 15. Obtained from the bottom of the first distillation column 1 through line 11 was MMA, which was free of water and low boiling-point components but contained MAA and high boiling-point components in small amounts. High-purity MMA was successfully furnished by subjecting the thus-obtained MMA to rectification (not shown).

A 20% aqueous solution of sodium hydroxide was supplied to the hydrolysis tank 5 through a line 16, so that the water phase was maintained there at pH 13-13.5 and room temperature for 30 minutes. The thus-hydrolyzed water phase was supplied through a line 17 to a middle stage of a second distillation column 6 (inner diameter: 80 mm; height: 5 m; packings: ¼″ Berl saddles). Heat was supplied at the base of column 6 through heat exchanger or reboiler 7. The water phase was distilled under normal pressure at a top temperature of 64° C., a bottom temperature of 100° C. and a reflux ratio of 4, whereby a methanol fraction 21 substantially free of MA and MP was recovered through line 19 and was condensed in condenser 8. The condensate from condenser 8 was stored in tank 9 and was divided into a reflux and a distillate. The reflux was returned to column 6 through line 21. The aqueous bottom fractions, which were essentially methanol-free could be withdrawn from the base of column 6 through line 18. In Table 1, the liquid quantities delivered through principal lines are shown for respective components.

TABLE 1

| Component | Line No. | | | | | | | | |
|---|---|---|---|---|---|---|---|---|---|
| | 10 | 11 | 13 | 14 | 15 | 16 | 17 | 18 | 21 |
| Water | 650 | — | 2500 | 20 | 3150 | 32 | 3182 | 3140 | 42 |
| Methanol | 930 | — | — | 40 | 930 | — | 935 | trace | 935 |
| MA | 12 | trace | — | 330 | 12 | — | trace | — | trace |
| MP | 3 | trace | — | 80 | 3 | — | trace | — | trace |
| MAA | 5 | 5 | — | — | — | — | — | — | — |
| MMA | 20000 | 19995 | — | 270 | 5 | — | 3 | — | 3 |
| Hexane | — | — | — | 30000 | — | — | — | — | — |
| NaOH | — | — | — | — | — | 8 | 20* | 20* | — |
| Total | 21600 | 20000 | 2500 | 30740 | 4100 | 40 | 4140 | 3160 | 980 |

*Sodium salt., Unit: g/hour.

What is claimed is:

1. A process for the purification of methyl methacrylate, which comprises the following steps:
   azeotropically distilling, together with hexane, a mixture comprising water, methanol and methyl methacrylate as principal components and containing at least one of methyl acrylate, methyl propionate and methacrylic acid, thereby obtaining a high boiling-point fraction and a low boiling-point fraction, said high boiling-point fraction being substantially free of water, methanol, methyl acrylate, methyl propionate and hexane and composed principally of methyl methacrylate, and said low boiling-point fraction being principally composed of water, methanol and hexane and containing at least one of methyl acrylate and methyl propionate;
   cooling the low boiling-point fraction to obtain a condensate;
   separating the condensate into a water phase and an oil phase;
   adding an alkaline substance to the water phase;
   distilling the water phase containing alkaline substance, thereby recovering methanol; and
   using the oil phase as a source of hexane in the azeotropic distillation.

2. The process of claim 1, wherein the condensate is separated into the water phase and oil phase after addition of water to the condensate.

3. The process of claim 1, wherein t:e alkaline substance is sodium hydroxide or potassium hydroxide.

4. The process of claim 1, wherein the low boiling-point fraction is separated in a range of 37°-63° C. upon conducting the azeotropic distillation.

5. The process of claim 1, wherein in the azeotropic distillation, hexane is used in an amount at least equal to the sum of a 17-fold amount by weight of water and a 3-fold amount of methanol but not greater than the sum of a 50-fold amount by weight of water and a 10-fold amount of methanol.

6. A process for the preparation of methyl methacrylate, which comprises the following steps:

esterifying with methanol at least one methacrylic compound selected from the group consisting of methacrylic acid and methacrylamide, thereby obtaining a mixture comprising water, methanol and methyl methacrylate as principal components and containing at least one of methyl acrylate, methyl propionate and methacrylic acid;

azeotropically distilling the mixture together with hexane, thereby obtaining a high boiling-point fraction and a low boiling-point fraction, said high boiling-point fraction being substantially free of water, methanol, methyl acrylate, methyl propionate and hexane and composed principally of methyl methacrylate, and said low boiling-point fraction being principally composed of water, methanol and hexane and containing at least one of methyl acrylate and methyl propionate;

cooling the low boiling-point frac&:ion to obtain a condensate;

separating the condensate into a water phase and an oil phase;

adding an alkaline substance to the water phase;

distilling the water phase containing alkaline substance, thereby recovering methanol; and using the oil phase as a source of hexane in the azeotropic distillation.

7. The process of claim 6, wherein in the azeotropic distillation, hexane is used in an amount at least equal to the sum of a 17-fold amount by weight of water and a 3-fold amount of methanol but not greater than the sum of a 50-fold amount by weight of water and a 10-fold amount of methanol.

* * * * *